United States Patent
Kuo (10) Patent No.: US 9,241,542 B2
(45) Date of Patent: Jan. 26, 2016

(54) BUCKLE

(71) Applicant: Yen-Ting Kuo, Hsin Kang Township, Chiayi County (TW)

(72) Inventor: Yen-Ting Kuo, Hsin Kang Township, Chiayi County (TW)

(73) Assignee: Shine Ball Enterprise Co., Ltd., Chiayi County (TW)

( * ) Notice: Subject to any disclaimer, the term of this patent is extended or adjusted under 35 U.S.C. 154(b) by 234 days.

(21) Appl. No.: 14/076,309

(22) Filed: Nov. 11, 2013

(65) Prior Publication Data
US 2015/0128385 A1    May 14, 2015

(51) Int. Cl.
| | |
|---|---|
| A44B 11/00 | (2006.01) |
| A44B 17/00 | (2006.01) |
| A61F 9/02 | (2006.01) |
| A63B 33/00 | (2006.01) |
| A44B 11/08 | (2006.01) |
| B63C 11/12 | (2006.01) |

(52) U.S. Cl.
CPC ............ *A44B 11/006* (2013.01); *A44B 17/0011* (2013.01); *A61F 9/027* (2013.01); *A44B 11/08* (2013.01); *A63B 33/002* (2013.01); *B63C 2011/128* (2013.01); *Y10T 24/4077* (2015.01)

(58) Field of Classification Search
CPC .. A44B 11/006; A44B 17/0011; A44B 11/08; A61F 9/027; A63B 33/002; Y10T 24/4016; Y10T 24/4072
See application file for complete search history.

(56) References Cited

U.S. PATENT DOCUMENTS

| | | | |
|---|---|---|---|
| 2011/0030179 A1* | 2/2011 | Shiue | 24/594.11 |
| 2011/0138588 A1* | 6/2011 | Shiue | 24/628 |
| 2013/0074249 A1* | 3/2013 | Chou | 2/448 |

* cited by examiner

*Primary Examiner* — Robert J Sandy
(74) *Attorney, Agent, or Firm* — Alan D. Kamrath; Kamrath IP Lawfirm, P.A.

(57) ABSTRACT

A buckle includes a base that receives therein a pressing board having a front end pivotally coupled to the base and a rear end provided with a clutch portion for clutching a tooth of a head strap, and an operating member that is received in the base and corresponds to a back of the pressing board. The operating member has two buttons. When an arcuate bar pressing against the operating member is pressed inward, the arcuate bar deforms and pushes the pressing board to swing outward, making the clutch portion disengage from the tooth of the head strap, so that length adjustment of the head strap is allowed. After the adjustment, the pressing board automatically swings back due to the tension of the head strap, so that the clutch portion clutches another tooth of the head strap to position the head strap.

4 Claims, 8 Drawing Sheets

BUCKLE

BACKGROUND OF THE INVENTION

1. Technical Field
N/A
2. Description of Related Art

The present invention relates to a buckle allowing easy length adjustment of a head strap. The buckle primarily comprises a base, a pressing board that is engaged with the base and has a swingable rear end, and an operating member engaged with the base, such that the operating member is aligned with the back of the pressing board and two buttons of the operating member are jutting out of the base, while an arcuate bar linking the two buttons presses against the back of the pressing board. Thus, a user can use his/her two fingers' opposite, inward, small movements, which press the two buttons inward the base, to make the arcuate bar push the rear end of the pressing board outward, in turn easily causing a clutch portion at the rear end of the pressing board to depart from a tooth formed on the head strap which it originally clutches.

BRIEF SUMMARY OF THE INVENTION

Conventionally, people wear swimming goggles and diving goggles when they go swimming, snorkeling or diving for eye protection and clear vision underwater. In use, it is important to ensure the swimming goggles or diving goggles fit the user's face in a watertight way. Taking a pair of diving goggles for example, the frame of the goggle has to be one conforming to the user's face shape. For making a selection, one can press the goggle against his/her face, inhale air from the nose, and then remove their hands from the goggles. An acceptable pair of goggles shall at this time remain closely attached to the face. The existing diving goggles typically have their skin-contacting portions made of silicone, making the goggles more comfortable and durable than their predecessors made of rubber.

As a reliable approach to affixing swimming goggles and diving goggles on users' faces, a head strap is provided to hold the back of the user's head. As such a head strap is tensed by pulling two ends thereof backward, so that the swimming goggles or diving goggles can be secured on the face with enhanced watertightness. The head strap has to be properly adjusted in terms of length (compression to the head) to have the lengths at two sides equal, and to allow two fingers to be inserted between the head strap and the user's head with the fingers feeling slightly pressed yet comfortable. If the head strap is excessively loose, the swimming goggles or diving goggles tend to come off from the user's face. On the contrary, an excessively tight head strap may be the reason of a headache or ocular pain.

The ways and levels of convenience of head strap adjustment vary from one manufacturer to another. For example, U.S. Pat. No. 8,407,820 implements a buckle to combine a pair of swimming goggles with a head strap. The buckle allows adjustment of the head strap in terms of length (compression to the head). The scheme used therein is a buckle including a base to which a head strap is attached and a pressing board having a front end engaged with the base. The pressing board has its rear end free and bendable. The base receives an operating button that has two buttons exposed outside two sides of the base and an arcuate portion plate formed between the two buttons. Two pressing surfaces are formed at inner ends of the two buttons facing each other, while two inclined guiding faces are formed on the back of the pressing board for abutting against the pressing surfaces. In addition, at the back of the rear end of the pressing board, a clutch portion is provided for engaging with teeth formed on the head strap, to hold the head strap in position.

To adjust the head strap, a user has to use his/her fingers to push the buttons at the two ends of the operating button into the base, so that the pressing surfaces push the inclined guiding faces at the back of the pressing board outward, making the pressing section at the rear end of the pressing board disengage from the tooth of the head strap, thereby allowing length adjustment of the head strap. After adjustment and once the fingers release the operating button, the pressing board presses the pressing section to return and combine with one of the teeth of the head strap, so that the head strap can be held at the adjusted length.

While the known scheme is easy to implement and involves only a simple structure, it uses the pressing and displacement happening between the pressing surfaces of the operating button and the inclined guiding faces of the pressing board, so the user's fingers have to exert more effort and move a longer distance to make the pressing section of the pressing board depart from the tooth of the head strap, leaving the overall operation uncertain.

Moreover, as the pressing surfaces of the operating button and the inclined guiding faces of the pressing board abut and rub against each other, these components tend to become worn over time. When these components become worn, the buttons of the operating button have to be displaced for a longer distance to achieve the foregoing function, making the operation harder and more effort-consuming.

SUMMARY OF THE INVENTION

Hence, for improving the existing buckle that may have the problems of hard and effort-consuming operation, the present invention herein provides a buckle with improved operational convenience. The buckle has an arcuate bar provided between two buttons of an operating member that is received in a base, and the arcuate bar presses against the back of the pressing board. Thus, by merely pressing the two buttons slightly, the arcuate bar is deformed and displaced significantly, to allow a clutch portion of the pushed pressing board to disengage from a tooth of a head strap. Thereby, the buckle-releasing operation is easier, and all potential operational problems related to worn components can be eliminated.

For solving its technical issues, the present invention adopts a scheme including a buckle allowing a head strap that has successively aligned and spaced teeth to be wound therearound. The buckle includes a base that allows the head strap to be attached thereto and receives therein a pressing board and an operating member. The base has a shell-like body having a shaft formed at a rear end thereof that allows the head strap to be wound therearound, and having openings oppositely provided at two sides thereof. The pressing board is received in the base with a side thereof exposed outside, and has a clutch portion formed at a back of a rear end thereof for clutching one of the teeth of the head strap. The operating member has two opposite buttons that are received in the two openings and jutting out of the two sides of the base, and has an arcuate bar linking the two buttons and pressing against the back of the pressing board.

In the above-described scheme of the present invention, an engaging portion is vertically raised from the back of the pressing board at a front end thereof for passing through the base.

In the above-described scheme of the present invention, an insertion hole is formed at a bottom of the base, and two opposite sliding blockers are provided close to inner sides of the two buttons for being slidably received in the insertion hole.

In the above-described scheme of the present invention, a protuberance is formed on an inner surface of a front end of the base, and retaining sockets are oppositely provided near the front end of the base. A recess is formed at a front end of the pressing board for fittingly receiving the protuberance, and two opposite hooks are provided at two sides of the pressing board near a front end thereof for being retained in the retaining sockets.

Since the arcuate bar between the two buttons of the operating member as disclosed in the present invention exerts force perpendicularly on the back of the pressing board, the fingers can press the buttons with less effort and such a configuration eliminates all potential operational problems related to worn components. Furthermore, as it requires just a small displacement of the two buttons to make a large bending deformation of the arcuate bar, the user can feel improved hand touch during operation, making the adjustment of the head strap more pleasing.

DETAILED DESCRIPTION OF THE INVENTION

Figure 1:
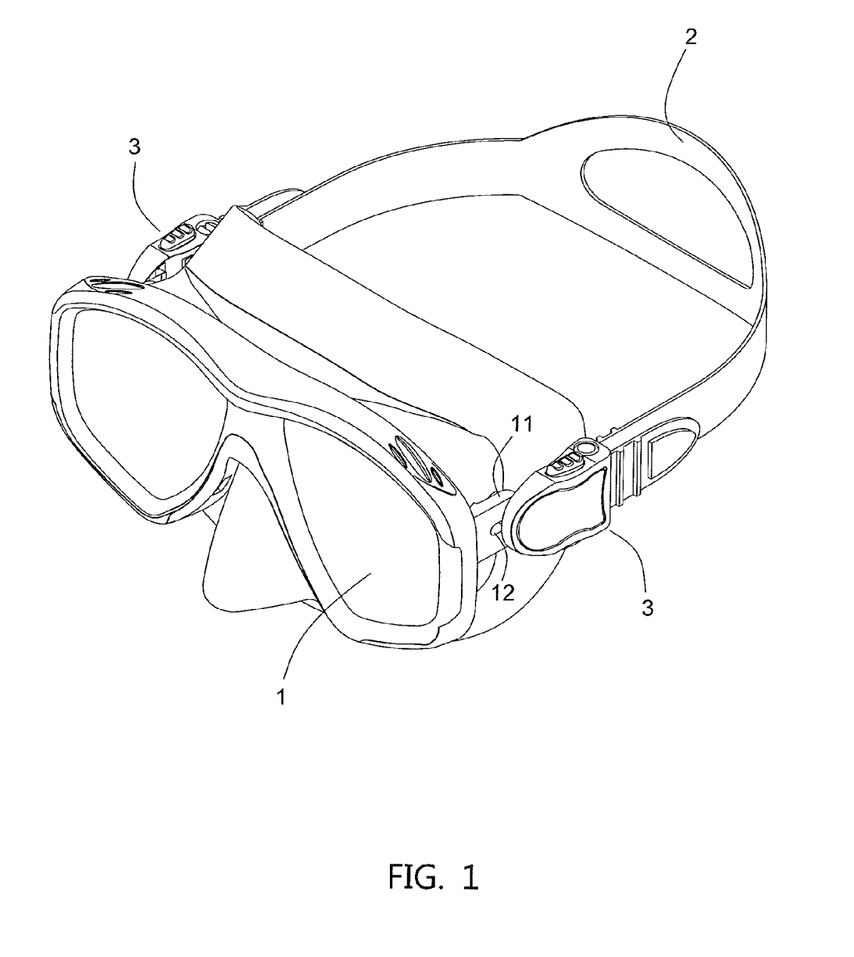
FIG. 1 is a schematic drawing showing a buckle of the present invention assembled to diving goggles.
Figure 2:
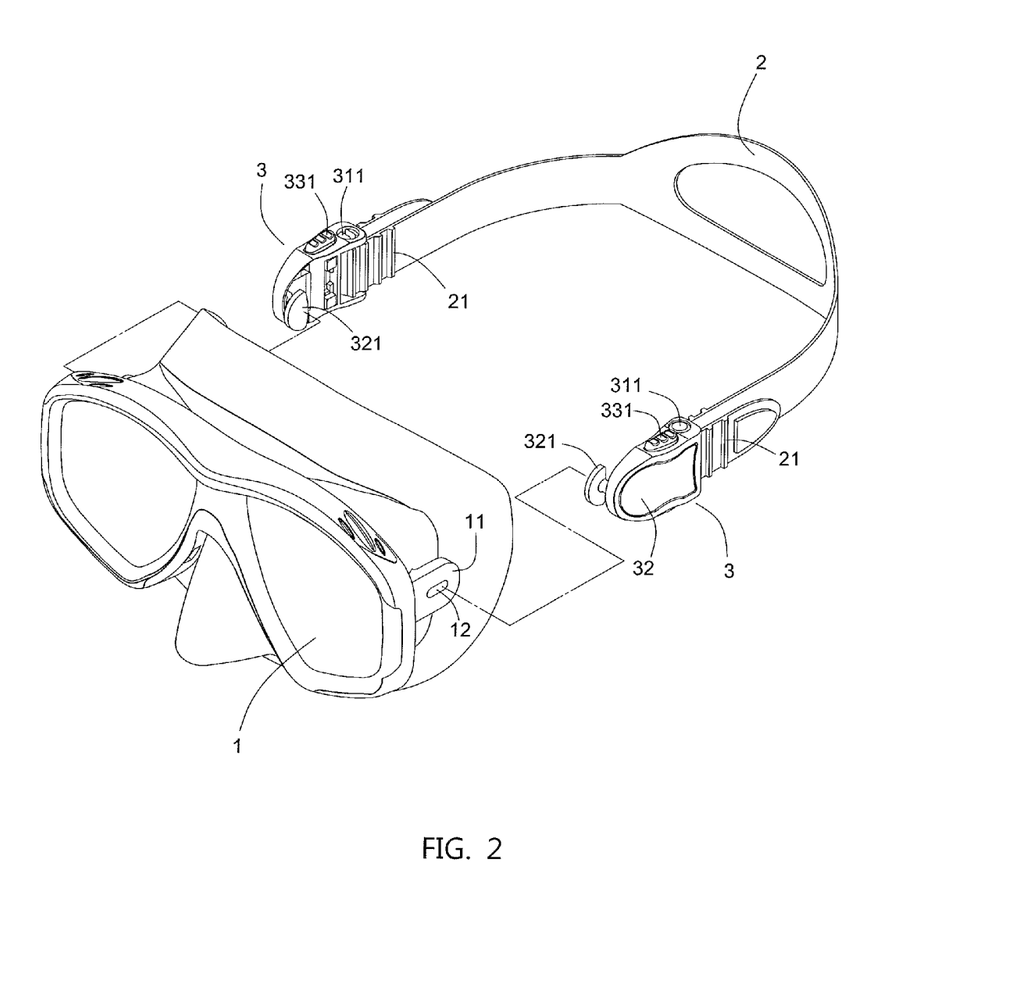
FIG. 2 is a schematic drawing, according to FIG. 1, showing the buckle disassembled from the diving goggles.

Referring to FIG. 1 and FIG. 2, the buckle 3 of the present invention is applied to, for example, a pair of diving goggles 1. The diving goggles 1 has its two opposite sides provided with ear portions 11 each having an engaging hole 12, and a head strap 2 with each of its two ends attached to a buckle 3. The configuration of the buckle 3 and how the buckle 3 is engaged with the head strap 2 will be described in detail below. The buckle 3 has an engaging portion 321 to pass through the engaging hole 12 to attach the buckle 3 to the diving goggles 1.

Please refer to FIG. 3 through FIG. 5 and FIG. 7 for the configuration of the buckle 3 and its relationship with the head strap 2. As shown, the head strap 2 has two ends, with each of which has a surface formed with successively aligned and spaced teeth 21. The buckle 3 has a shell-like base 31 with its outer side open, a pressing board 32 received in the open part of the base 31 with its one end swingable, and an operating member 33 installed in the base 31 for pressing against the pressing board 32 at its back. A shaft 311 is provided at a rear end of the base 31 for the head strap 2 to be wound therearound. An insertion hole 313 is formed at the bottom of the base 31 near its center, and two openings 312 are oppositely formed on the base 31 to flank the insertion hole 313. Furthermore, retaining sockets 314 are oppositely provided near the front end of the base 31, while a protuberance 315 is formed on the inner surface of the front end of the base 31 aligned with the central line of the base 31.

Figure 3:
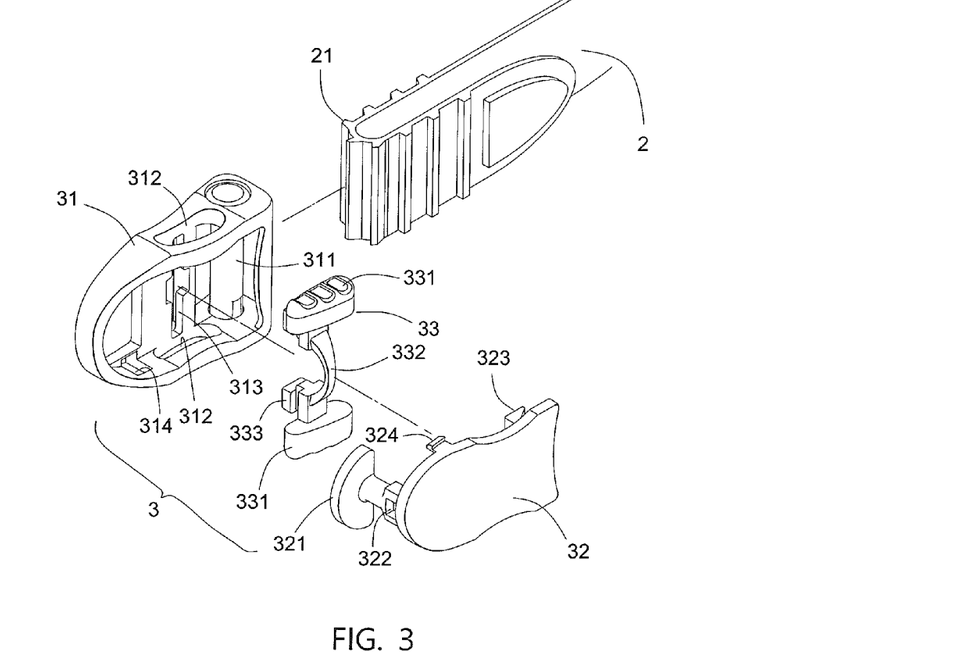
FIG. 3 is an exploded view of the buckle of the present invention, showing its relationship with the head strap.
Figure 4:
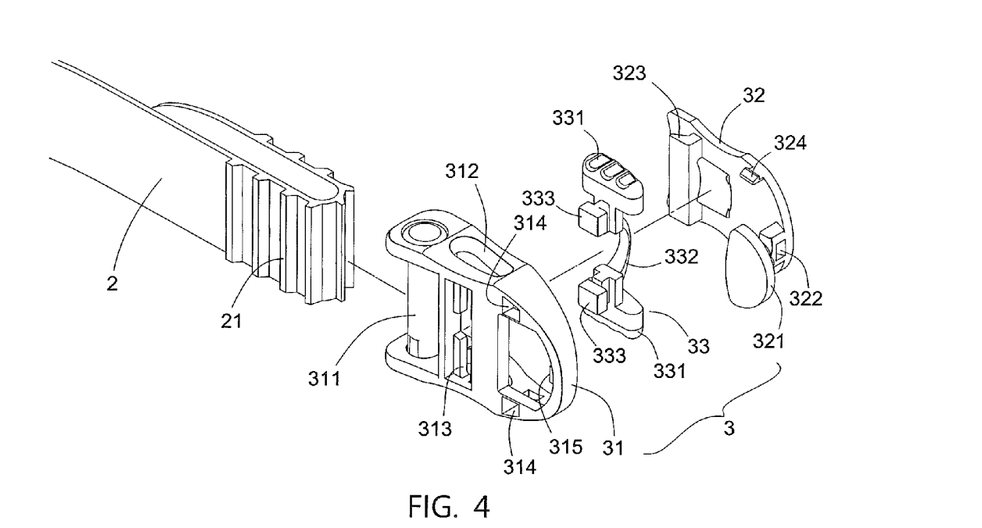
FIG. 4 is another exploded view of the buckle of the present invention, showing its relationship with the head strap.
Figure 5:
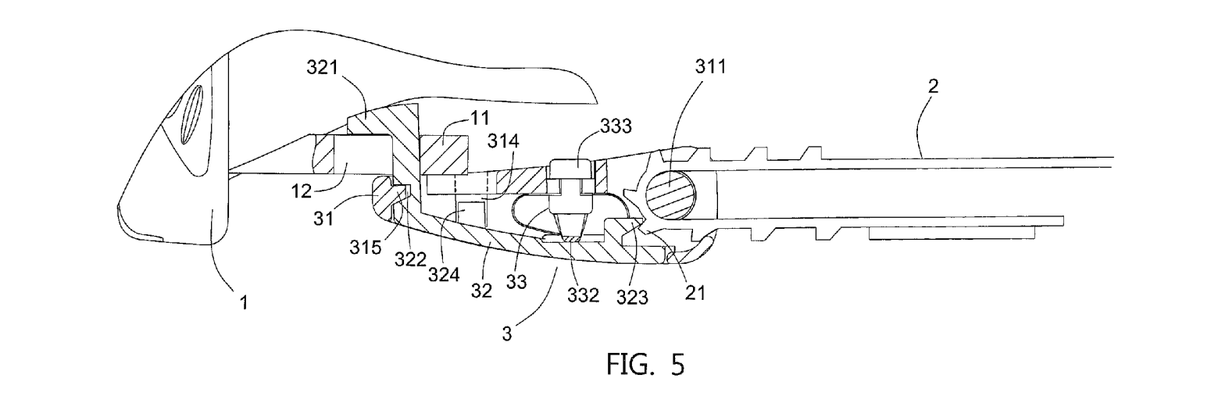
FIG. 5 is a cross-sectional, top view of the buckle of the present invention engaged with the head strap.

The above-mentioned engaging portion 321 is vertically raised from the back of the front end of the pressing board 32 for passing through the base 31 and then getting retained by the engaging hole 12 of the ear portion 11 at either side of the diving goggles 1. At the center part of the front end of the pressing board 32, a recess 322 is formed for fittingly receiving the protuberance 315 of the base 31. The pressing board 32 further has two opposite hooks 324 at its two sides near the front end for being movably received in the retaining sockets 314 of the base 31, so that the pressing board 32 can be secured on the base 31 by virtue of its recess 322 and hooks 324. The pressing board 32 has its front end swingable against the base 31 when using the protuberance 315 of the base 31 as a pivot, allowing the pressing board 32 to stay close to or swing away from the base 31. A clutch portion 323 is provided at the back of the pressing board 32 for engaging with the teeth 21 of the head strap 2.

Figure 7:
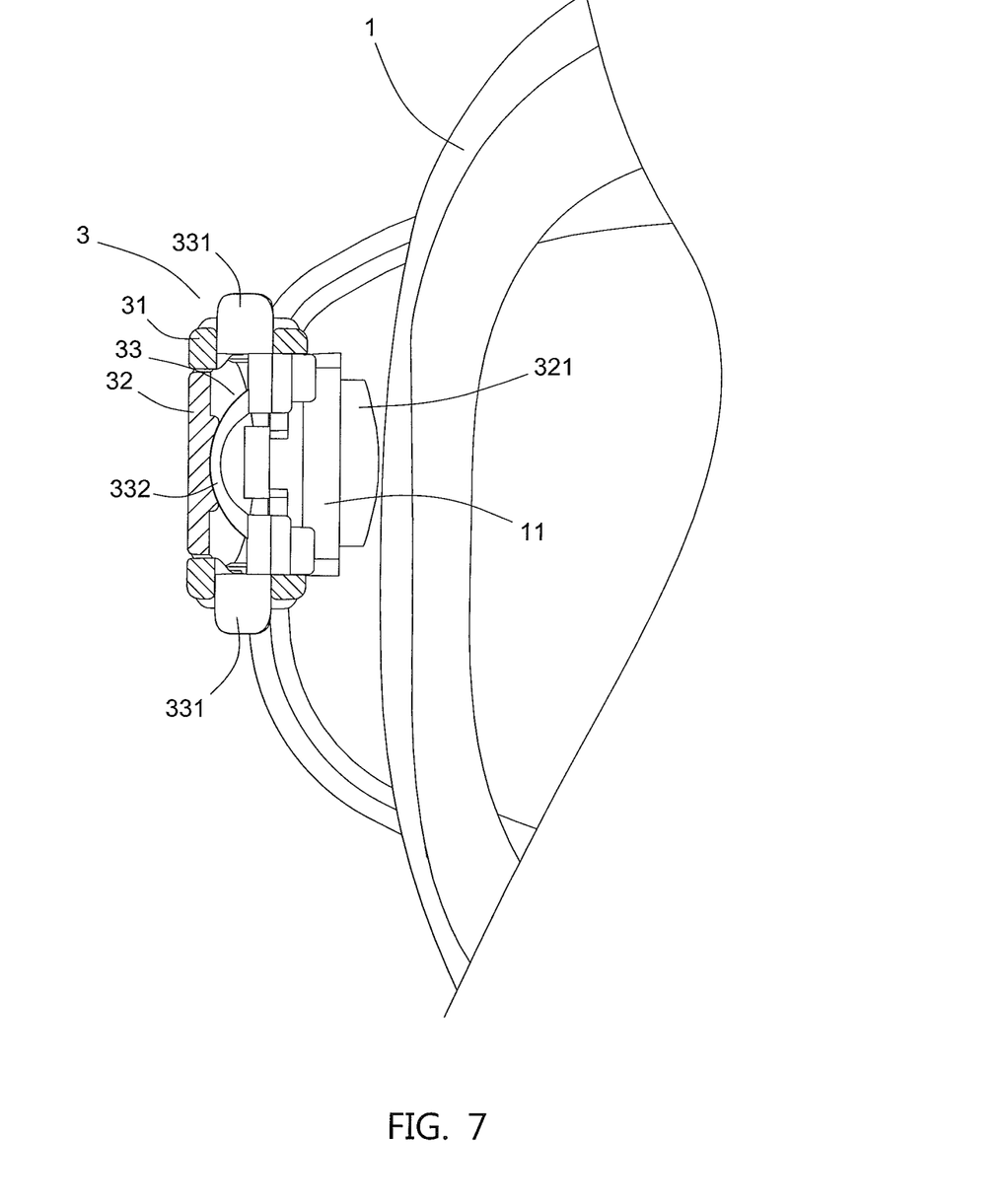
FIG. 7 is a cross-sectional, rear view of the buckle of the present invention, particularly showing the operating member.

The operating member 33 has two opposite buttons 331 for passing through the openings 312 and then jutting out of the two sides of the base 31. An arcuate bar 332 links the two button 331 and presses against the back of the pressing board 32, while two opposite sliding blockers 333 are provided corresponding to the inner sides of the two buttons 331. The two sliding blockers 333 can be slidably received in the insertion hole 313 of the base 31 without the risk of falling out. The arcuate bar 332 normally uses the outward bias of its two ends to expose the two button 331 at the openings 312 of the base 31. When the two buttons 331 are pressed inward, the arcuate bar 332 is compressed and deforms to become more arcuate.

Figure 6:
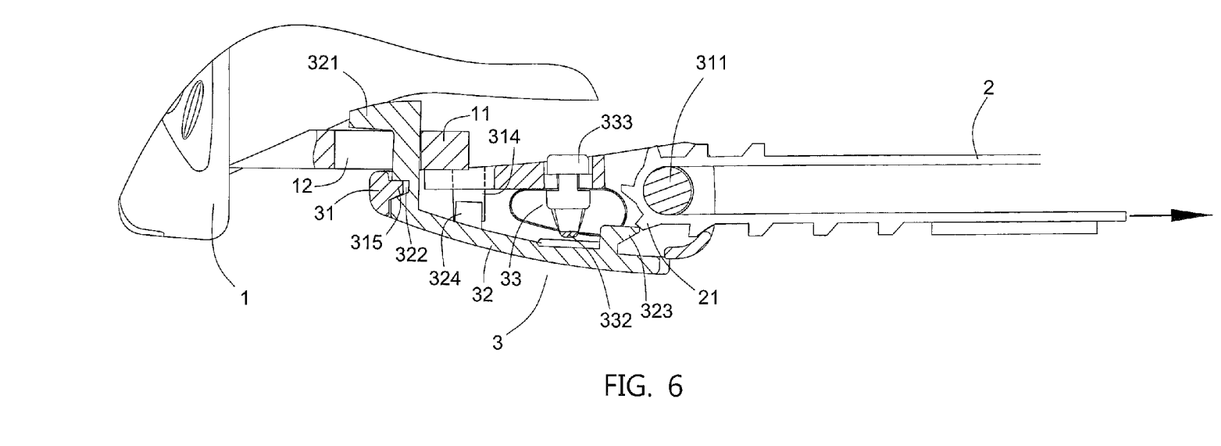
FIG. 6 depicts movement of the pressing board in response to a pull-back of the end of the head strap.

Therefore, as shown in FIG. 5, the head strap 2 first has its toothed end wound around the shaft 311 at the rear end of the base 31, and the clutch portion 323 at the rear end of the pressing board 32 of the buckle 3 clutches the corresponding tooth 21 of the head strap 2. When being worn on a user's head, the head strap 2 is tensed by the head and gets positioned to maintain the close engagement with the buckle 3. In the event that the head strap 2 is too loose with respect to the user's head, as shown in FIG. 6, the user can pull the end of the head strap 2 backward to make the teeth 21 of the head strap 2 prop up and pass the clutch portion 323 at the rear end of the pressing board 32 one by one, until the head strap 2 reaches a proper length. Upon release of the user's pulling force and as a result of that the tensed head strap 2 pulls the base 31 backward and in turn drives the engaging portion 321 of the pressing board 32 to counteract that pulling force, so that the rear end of the pressing board 32 automatically swings back against the recess 322 of the pressing board 32 to engage the clutch portion 323 with another tooth 21 of the head strap 2.

Figure 8:
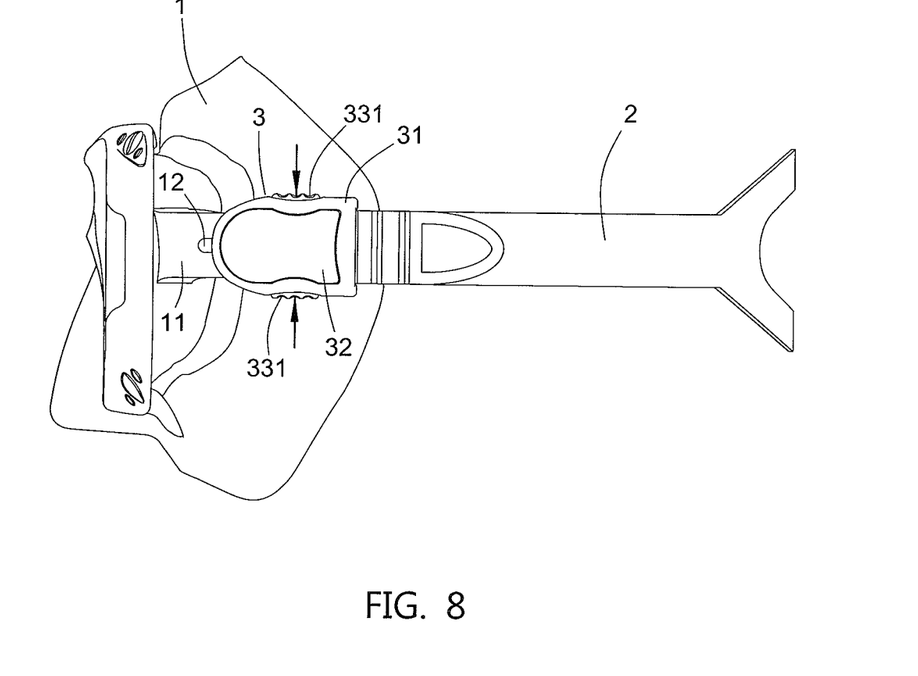
FIG. 8 is a side view of the buckle of the present invention assembled to the goggles, showing the operating member getting pressed.
Figure 9:
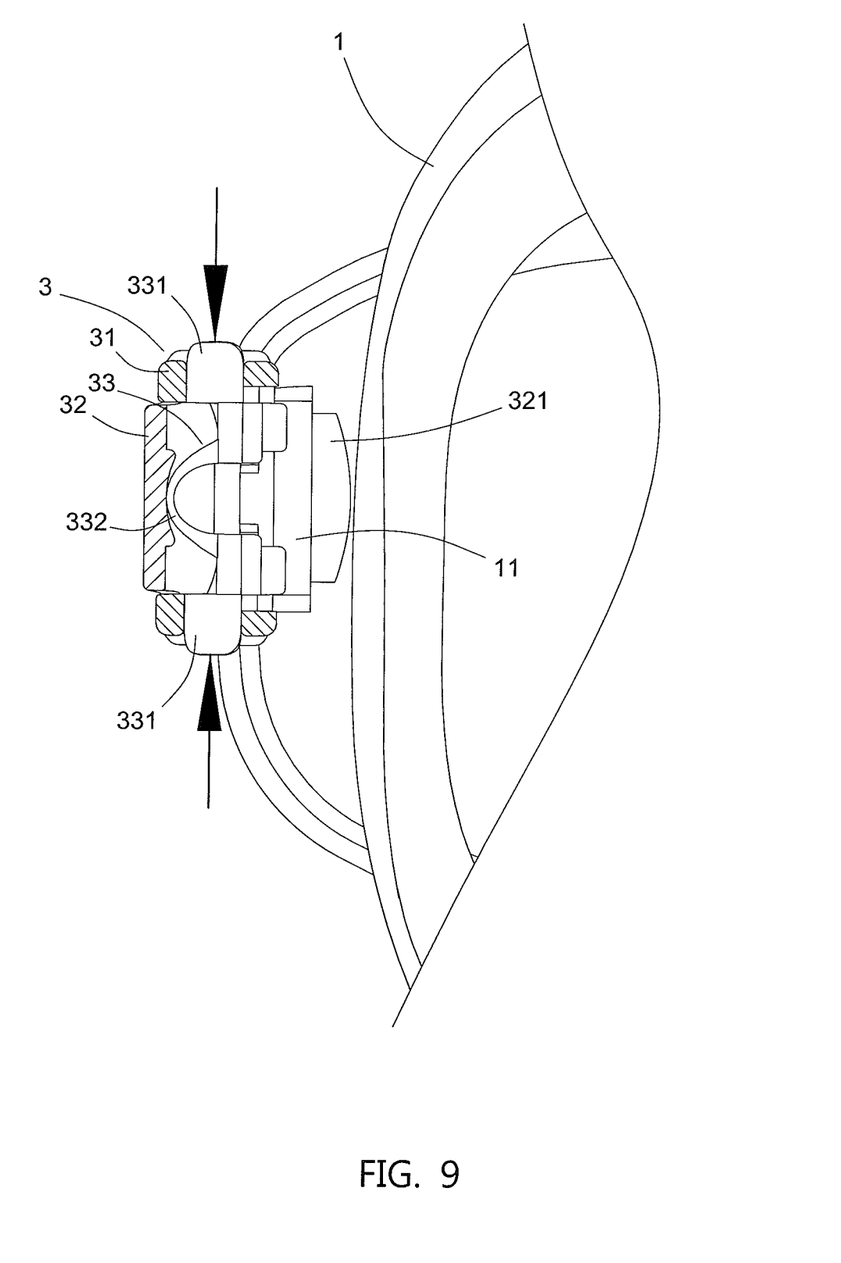
FIG. 9 is a cross-sectional, rear view of the buckle of the present invention, particularly showing the pressed operating member pushing the pressing board.
Figure 10:
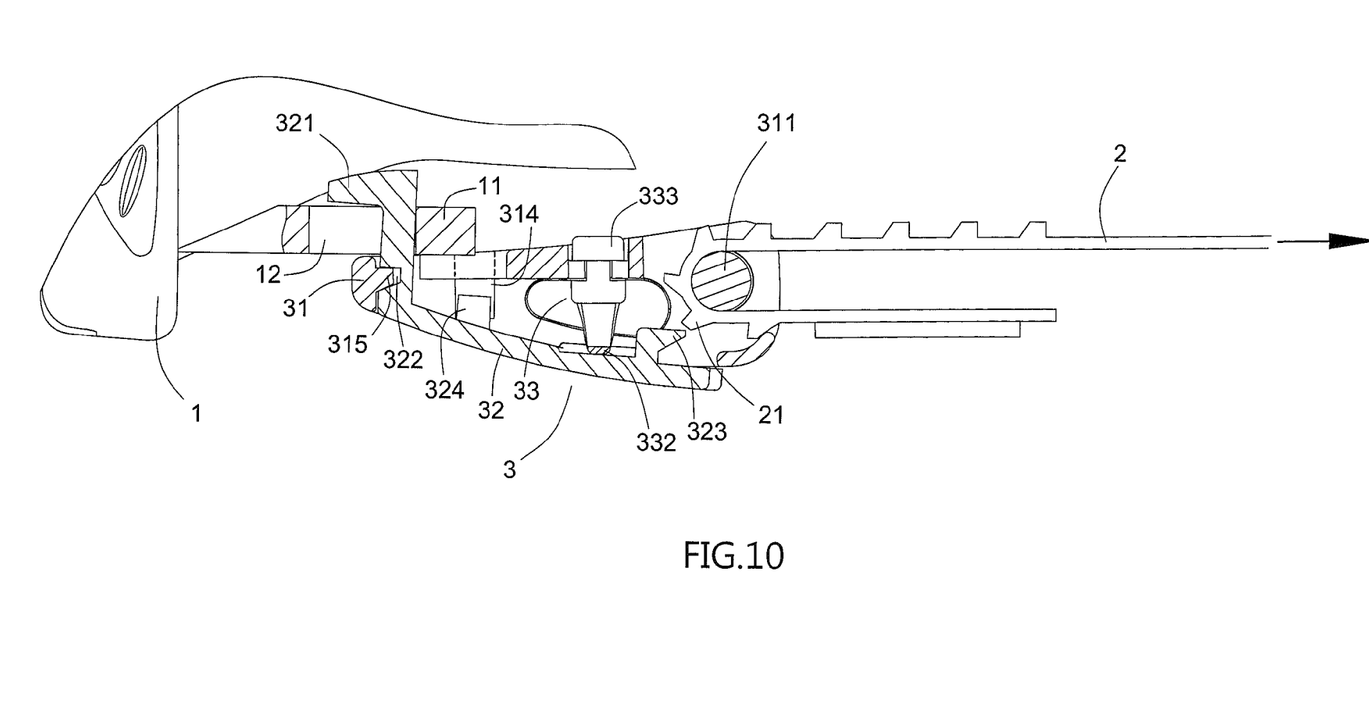
FIG. 10 illustrates adjustment of the head strap when the buckle of the present invention is released.

In the event that the head strap 2 is excessively tight, referring to FIG. 8 through FIG. 10, the user can use his/her two fingers to simultaneously press the two buttons 331 of the operating member 33 inward, making the two buttons 331 retract into the base 31, in turn causing the arcuate bar 332 between the two button 331 to become more arcuate and thus push the rear end of the pressing board 32 to swing outward. At this time, the clutch portion 323 at the rear end of the pressing board 32 departs from the tooth 21 of the head strap 2, and the head strap 2 can freely move inward or outward on the shaft 311. When the head strap 2 is adjusted to the proper length and the user releases the head strap 2 again, and as a result of that the tensed head strap 2 pulls the base 31 backward and in turn drives the engaging portion 321 of the pressing board 32 to counteract that pulling force, so that the rear end of the pressing board 32 automatically swings back against the recess 322 of the pressing board 32 to engage the clutch portion 323 with another tooth 21 of the head strap 2.

Hence, with the arcuate bar 332 of the operating member 33 received in the base 31 of the buckle 3, and by merely pressing the two buttons 331 slightly, the arcuate bar 332 is deformed and displaced significantly, to allow the clutch portion 323 of the pushed pressing board 32 to easily disengage from the tooth 21 of the head strap 2, providing the user with improved hand touch during operation. Additionally, when the two buttons 331 of the operating member 33 are pressed by the user's fingers simultaneously, the arcuate bar 332 exerts an almost perpendicular force onto the pressing board 32 to push it, so the user can perform such operation with less effort and more convenience. Meanwhile, all potential operational problems related to worn components as seen in the prior art can be eliminated.

What is claimed is:

1. A buckle to which a head strap having successively aligned and spaced teeth is attached, with the buckle configured to be assembled to a pair of diving goggles, comprising:
    a base having a shell-like body, with a shaft formed at a rear end of the base that allows the head strap to be wound therearound, and with two openings oppositely provided at two sides of the base;
    a pressing board received in the base, with a side of the pressing board exposed outside, and with a clutch portion formed at a back of a rear end of the pressing board clutching one of the teeth of the head strap; and
    an operating member having two opposite buttons received in the two openings and jutting out of the two sides of the base, and having an arcuate bar linking the two buttons and pressing against the back of the pressing board, wherein an insertion hole is formed at a bottom of the base, and wherein two opposite sliding blockers are provided close to inner sides of the two buttons and slidably received in the insertion hole.

2. The buckle of claim 1, wherein an engaging portion is vertically raised from the back of the pressing board at a front end thereof for passing through the base.

3. A buckle to which a head strap having successively aligned and spaced teeth is attached, with the buckle configured to be assembled to a pair of diving goggles, comprising:
    a base having a shell-like body, with a shaft formed at a rear end of the base that allows the head strap to be wound therearound, and with two openings oppositely provided at two sides of the base;
    a pressing board received in the base, with a side of the pressing board exposed outside, and with a clutch portion formed at a back of a rear end of the pressing board clutching one of the teeth of the head strap; and
    an operating member having two opposite buttons received in the two openings and jutting out of the two sides of the base, and having an arcuate bar linking the two buttons and pressing against the back of the pressing board, wherein a protuberance is formed on an inner surface of a front end of the base, wherein retaining sockets are oppositely provided near the front end of the base, wherein a recess is formed at a front end of the pressing board and fittingly receiving the protuberance, and wherein two opposite hooks are provided at two sides of the pressing board near a front end thereof and retained in the retaining sockets.

4. The buckle of claim 3, wherein an engaging portion is vertically raised from the back of the pressing board at a front end thereof for passing through the base.

* * * * *